United States Patent [19]

Morrison et al.

[11] Patent Number: 5,211,888
[45] Date of Patent: May 18, 1993

[54] CATALYZED HYDROCARBYLLITHIUM PROCESS

[75] Inventors: Robert C. Morrison, Gastonia; Randy W. Hall, Kings Mountain; James A. Schwindeman, Charlotte; Conrad W. Kamienski, Gastonia; John F. Engel, Belmont, all of N.C.

[73] Assignee: FMC Corporation, Philadelphia, Pa.

[21] Appl. No.: 842,944

[22] Filed: Feb. 27, 1992

Related U.S. Application Data

[63] Continuation-in-part of Ser. No. 736,660, Jul. 26, 1991, abandoned.

[51] Int. Cl.$^5$ ............................ C07F 1/02; C07F 3/02; C07F 3/04
[52] U.S. Cl. ................................................. 260/665 R
[58] Field of Search ..................... 260/665 R

[56] References Cited

U.S. PATENT DOCUMENTS

| | | | |
|---|---|---|---|
| 3,085,118 | 4/1963 | Foster | 260/665 R |
| 3,193,590 | 7/1965 | Hsieh | 260/665 R |
| 3,293,313 | 12/1966 | Borkowski | 260/665 R |
| 3,420,903 | 1/1969 | Smith . | |
| 4,593,112 | 6/1986 | Takamizawa . | |
| 4,814,474 | 3/1989 | Shirahata . | |

OTHER PUBLICATIONS

Journal of Organometallic Chemistry, vol. 326 (1987) pp. 1–7 by Lochmann and Trekoval.

W. Novis Smith, *Journal of Organometallic Chemistry*, 82, pp. 1–6, Jan. 1969.
A. Shirahata, *Tetrahedron Letters*, vol. 30, No. 46, pp. 6393–6394, Mar. 1989.

*Primary Examiner*—José G. Dees
*Assistant Examiner*—Joseph M. Conrad, III
*Attorney, Agent, or Firm*—C. C. Fellows; R. L. Andersen; Robert C. Morrison

[57] ABSTRACT

A catalytic process for alkylating an alkali metal selected from lithium, sodium and potassium with an alkyl halide containing 3 to 20 carbon atoms comprising conducting the reaction in the presence of a catalytic compound represented by the formula $$(RR^1R^2M^a)_yA(R^3)_x$$

wherein R, $R^1$ and $R^2$ are independently selected from hydrogen, halogen, alkyl, alkenyl, cycloalkyl, and aryl groups, $R^3$ is independently selected from aryl groups containing 6 to 18 carbon atoms, four to six-membered heterocyclic carbon containing groups containing one to two hetero atoms selected from oxygen, nitrogen, and sulfur; hydroxyalkyl, alkoxyalkyl and monoalkylaminoalkyl and dialkylaminoalkyl groups containing 2 to 13 carbon atoms; $M^a$ is selected from silicon, carbon, germanium, and tin, A is selected from oxygen, sulfur, nitrogen and phosphorus, and x and y independently have values from zero to three.

13 Claims, No Drawings

CATALYZED HYDROCARBYLLITHIUM PROCESS

This application is a continuation-in-part of U.S. Ser. No. 736,660 filed Jul. 26, 1991, now abandoned.

The preparation of organic solvent solutions of hydrocarbyllithium compounds is well known to the art and is disclosed in many patents and printed publications among which are, for example, U.S. Pat. No. 2,816,936, 2,865,969, 3,091,606, 3,122,592, 3,293,313, 3,420,903, and 3,452,112.

The most important of the hydrocarbyllithium compounds commercially are those produced in hydrocarbon solvents such as n-butyllithium, sec-butyllithium, and tert-butyllithium. These are generally produced by reaction of the corresponding alkyl halide, preferably an alkyl chloride, with lithium metal in hydrocarbon solvents $$R\text{-}Cl + 2Li \rightarrow RLi + LiCl$$

Yields of these hydrocarbyllithiums generally fall in the 70–90% range; and losses occur by competing side reactions of coupling and disproportionation:

$$R\text{-}Li + RCl \rightarrow R\text{—}R + LiCl \text{ (coupling)}$$

$$RLi + R\text{-}Cl \rightarrow RH + R'CH\text{=}CH_2 + LiCl \text{ (disp)}$$

(R' = R minus 2 carbons)
Methods to improve yields have been investigated by various workers but a high yield process for producing highly pure alkyllithium compounds is needed.

The present invention provides a process for producing alkyllithium compounds in improved yields by the reaction of lithium metal and alkyl halides in a hydrocarbon solvent in the presence of a catalytic amount of a compound exemplified by the formula:

$$(RR^1R^2M^a)_yA(R^3)_y$$

wherein R, $R^1$ and $R^2$ are independently selected from hydrogen, halogen, alkyl or alkenyl groups containing from one to thirteen carbon atoms; $M^a$ is a Group IV element selected from silicon, carbon, germanium and tin; A is selected from oxygen, sulfur, nitrogen and phosphorus; $x+y$ are equal to the valence of A; x and Y may independently have a value from zero to three. These substances, which may hereinafter be termed catalysts or protocatalysts, include bis-hydrocarbyl ethers, hydrocarbyl silyl ethers, bis-silyl ethers, tri-hydrocarbylamines, hydrocarbyl silyl amines, tris-organosilylamines, tris-organo germylphosphines and the like.

Some examples of compounds useful in the practice of this invention are as follows:

a. Hydrocarbyl ethers, such as, e.g., cyclic and acyclic ethers, symmetrical and unsymmetrical dialkyl, diaryl, and alkylaryl ethers which include, but are not limited to dimethyl ether, diethyl ether, tetrahydrofuran, methyl tetrahydrofuran, tetrahydropyran, anisole, methyl-t-butyl ether, di-n-butyl ether, diamyl ether, di-n-hexyl ether, di-n-octyl ether, butylphenyl ether, diphenyl ether and the like. Additional useful ethers are glycol ether types, such as the mono- and di- methyl, ethyl and butyl ethers of ethylene glycol, diethylene glycol, triethylene glycol, and the like. Also useful are acetals (1,1-ethers) such as dimethoxyethane and diethoxyethane. Preferred among these are the symmetrical and unsymmetrical dialkyl ethers, such as dimethyl ether, diethyl ether, di-n-butyl ether, di-n-hexyl ether, di-n-octyl ether, methyl-t-butyl ether and the like. Most preferred among these ethers is methyl-t-butyl ether. See Table 1.

b. Less preferred are hydrocarbylsilyl and bis-silyl ethers such as, e.g., t-butyldimethylisopropoxysilane, trimethylisopropoxysilane, chlorodimethylisopropoxysilane and hexamethyldisiloxane.

c. Tris-hydrocarbylamines such as, e.g., cyclic and acyclic tertiary amines including triethylamine, tri-n-butylamine, N,N,N',N'-tetramethylethylenediamine, pentamethyldiethylenetriamine, triethylenediamine, N-methylaniline, and the like. Like (b) above, these are also less preferred.

Although the catalysts or protocatalysts of this invention improve the yields of most alkyllithiums, some alkyllithium types are affected more than others. Thus, in the reaction of alkyl halide with lithium substrates to form alkyllithiums, those alkyl halides which possess sterically hindered carbon-halogen bonds appear to be more sensitive to the presence of the catalysts and show a much larger yield improvement versus no-catalyst runs than do those alkyl halides possessing more readily accessible carbon-halogen bonds. Sterically hindered alkyl halides are those possessing bulky groups or multiple groups surrounding the carbon-halogen bond; such as, e.g., a tertiary carbon-halogen bond like in tert-butyl chloride, or a primary or secondary carbon-halogen bond with nearby (alpha or beta) long chain alkyl substitution, such as, e.g., 2-ethylhexyl chloride or 2-methylbutyl chloride. Thus, alkyl halides catalyzed in their reaction with lithium metal to form the corresponding alkyllithiums, include but are not limited to (a) primary alkyl halides such as n-butyl chloride, n-hexyl chloride, n-octyl chloride, 2-ethylhexyl chloride and 2-methylbutyl chloride, (b) secondary alkyl halides such as isopropyl chloride, sec-butyl chloride, and cyclohexyl chloride and (c) tertiary alkyl halides such as tert-butyl chloride and tert-amyl chloride (see Table 2).

W. N. Smith in U.S. Pat. No. 3,420,903 taught that yields of tert-butyllithium in n-pentane could be improved from 40% to about 70–75% by the addition of small amounts of alcohols such as n-, sec-, or tert-butanol. We have substantiated these results and now, have further shown that the use of our ether catalysts materially improves on Smith's alcohol-catalyzed process (see Table 3). For example, the use of methyl tert-butyl ether as a catalyst produces yields of tert-butyllithium in pentane as high as 98% (essentially quantitative) (see also Table 2).

We have also found that as little as 0.2 mole % of an ether such as di-n-octyl or methyl tert-butyl ether need be used effectively to catalyze the reaction of lithium metal with tert-butyl chloride (see Table 4) whereas Smith teaches the use of about 0.6 to 2.5 mole % of a C4 alcohol or alkoxide.

This becomes important in the subsequent synthesis of an organometalloidal compound, such as, e.g., t-butyldimethylchlorosilane from the resulting tertbutyl-lithium, where a full mole % or more of an alcohol is required for best results, but only about 0.1–0.2 mole % of an ether is required (see our copending divisional application of U.S. Ser. No. 736660 filed on even date herewith.)

The use of much larger quantities of ether (10 to 100 mole % and higher based on the alkylchloride or alkyllithium employed) is detrimental to both processes (see Table 5) and drastically lowers the yield of the desired products. For example the yield of t-butyllithium is reduced from 95+% to 84% by increasing the MTBE catalyst from 1 mole % to 10 mole %. Although it is known in the art to produce alkyllithium compounds in such large amounts of ethers, the reactions must be carried out at very cold temperatures (below −35° C. for tert-butyllithium in diethyl ether) in order to prevent attack upon the ether by the tertbutyllithium, which temperatures are difficult to achieve on an industrial (plant) scale. The operating range for the ether catalysts of this invention is 0.1–10 mole %, based on alkyl halide with the preferred range being 0.5–2 mole % and the most preferred range being 0.8–1.2 mole %. Surprisingly, in the preferred range ethers are not readily cleaved, low operating temperatures are not required and the thermal stability of the hydrocarbon solution products of this invention are excellent.

A comparative sample, prepared according to Example 1 but with no added catalyst, is compared in Table 6 with catalyzed examples of this invention in a thermal stability study. Surprisingly, the most preferred example of this invention, MTBE, was as stable as the comparison which contained no ether.

Perhaps the most striking difference between the alcohol catalysts of W. N. Smith and the ether catalysts of our invention is evident when comparing the yields of tert-butyllithium achievable in higher boiling solvents than pentane. Smith, in J. Organometal. Chem., 82, (1974) 1–6, indicates that the maximum achievable yield of tert-butyllithium in hexane or hexane/isopentane is 30%. With our preferred ether catalyst, methyl tert-butyl ether, the yields in heptane approach those in pentane (about 90%) (see Table 4). Even di-n-octyl ether yields gives superior results (70%) to Smith. Again, W. N. Smith states that contacting the lithium metal with dilute t-butanol in hexane did not give an enhanced yield when subsequently reacted with t-butylchloride. On the other hand, we have found that our ether catalyst may be added either to the lithium metal or to the halide feed with good result (see examples 2 and 3).

The magnitude of the effect of an improved yield of tert-butyllithium on the cost of alkylating dimethyldichlorosilane to produce tertbutyldimethylchlorosilane can be seen in Table 7.

Because the raw material costs (RMC) shown for t-butyllithium represent a major percentage of the RMC for the resulting alkylated product, an appreciable rise in the latter's cost is effected by each 5% drop in the yield of tert-butyllithium. Thus, an 80% yield of tert-butyllithium adds almost 18% to the cost of the finished product when compared to a quantitative yield. This difference significantly affects the competitive edge which such a product would enjoy in the marketplace.

We have also unexpectedly found that soluble inorganic chloride levels in these alkyllithium solutions are significantly lower when our ether catalysts are used. Thus, for example, n-butyllithium produced without a catalyst generally contains 200–300 ppm of dissolved inorganic chloride (LiCl) whereas, with the MTBE catalyst, the value drops to less than 30 ppm. This is an advantage, in that solution clarity and quality is improved, and less interference occurs in reaction applications, such as in polymerization and organic synthesis.

Other factors important in synthesizing alkyllithium compounds are sodium content of the lithium metal, particle size of the lithium metal, surface condition of the lithium metal, and the use of sufficient excess lithium metal.

The sodium content of the lithium metal should be at least 0.5% by weight and preferably above 0.7%, and the particle size of the lithium metal below 200 microns, preferably below 100 microns. Although the best results are generally obtained with freshly prepared metal in those cases where no catalyst is used, the age or condition of the lithium metal surface is much less of a factor when a catalyst is employed.

The following examples further illustrate the invention.

EXAMPLE 1

Synthesis of t-Butyllithium Employing 1 mole percent of THF

A reactor equipped with a reflux condenser, and an addition funnel for adding liquid materials to the reactor, a temperature indicating device and means for stirring the reaction mass, was charged with 13.4 grams of lithium dispersion (1.94 moles), 165 milliliters of pentane, and 15 milliliters of a 1.5M solution of t-butyllithium in pentane. The lithium dispersion contained 0.74 wt. % alloyed sodium. The contents of the reactor were stirred for 1.5 hours in order to condition (activate) the lithium metal surface. Next, 65.03 grams of t-butylchloride (0.702 moles), 55 milliliters of pentane, and 0.48 grams of tetrahydrofuran (6.6 millimoles) were added to the addition funnel. The contents of the reactor were heated to reflux temperature (35° C.) by means of a heating mantle. The reaction was initiated by the addition of one milliliter of the diluted t-butylchloride as evidenced by a 1° C. rise in temperature, and an increase in reflux rate. The remaining diluted halide solution was added dropwise over the next two hours and four minutes while maintaining the reaction temperature at a constant reflux. During this time, a vigorous reaction ensued and no further heating was necessary. The reaction mass was stirred for an additional hour and a half, and then transferred to a glass filter funnel and filtered to obtain a clear, light yellow solution. The solid filtration residue was washed three times with 50 milliliter aliquots of pentane. The filtration residue washes were combined with the main filtrate solution. A total of 260.7 grams of a 15.5 wt. % solution of t-butyllithium solution was obtained. The recovered yield was 90.1% based on the amount of t-butylchloride employed.

EXAMPLE 2

Preparation of t-Butyllithium in Pentane Employing 1 mole percent Methyl tert-butyl Ether (MTBE)

To a reactor as described in example 1 under an argon atmosphere was added 14.15 g (2.04 m) lithium powder and 170 ml pentane. Next 10 ml of 1.8M t-butyllithium solution was added via syringe to the metal mixture and stirred at about 400 RPM's for at least 1 hour 20 minutes to condition the reactor and metal surface.

Meanwhile, to the dropping funnel was added 78.06 g (0.843 mole) t-butyl chloride, 70 ml pentane, and 0.794 g (0.00908 moles) MTBE. (Note: It is important to thoroughly mix the contents of the dropping funnel to give a uniform solution.) Before the addition of the t-butyl chloride solution, the lithium metal/pentane mixture was heated to near reflux (approx. 34° C.). About 1 ml of the t-butyl chloride feed solution was added at 32.0° C. which gave an exotherm in about 1 minute. After 3 minutes the reaction temperature began to fall and a dropwise addition of the feed solution was begun. (Note: Although a container was placed under the reactor for safety purposes, no cooling bath was employed. The exothermic reaction was run at reflux, which also cooled the reaction).

The total addition time was 2.0 hours. The maximum reflux temperature observed was 36.9° C. and the final reflux temperature was 36.0° C. at the end of the feed. The reaction mixture was stirred 2½ hours after the feed was complete.

This mixture was then pumped through a ⅜" teflon tube to a pressure filter (no filter aid) and filtered under an argon atmosphere. This filtration took 2 minutes. The reactor was then rinsed with 3×50 ml pentane each time and the rinses transferred to the muds in the filter which were also washed with the rinse and filtered. The final product was 281.1 g of hazy colorless solution. The haziness was caused by fine solids passing through the filter. Analysis of a clear sample of the solution indicated a 96.3% yield of active R-Li (18.49 wt %) and a 98.4% yield of total base (18.91 wt %) based on moles of t-butyl chloride added.

EXAMPLE 3

Preparation of t-Butyllithium in Pentane Employing 0.2 mole percent of Methyl tert-butyl Ether (MTBE) added to Metal To the reactor setup described in Example 1, under argon atmosphere, was added 14.12 g (2.03 moles) of lithium powder and 150 ml pentane. The lithium dispersion used in this reaction was the same as that used in Example 2. Next, 10 ml of 1.8M t-butyllithium solution was added via syringe to the metal mixture and stirred to condition the reactor and metal surface.

Meanwhile, to the dropping funnel was added 78.44 g (0.847 m) t-butyl chloride, and 85 ml pentane. (Note: It is important to thoroughly mix the contents of the dropping funnel to give a uniform solution.) Before beginning the addition of the t-butyl chloride feed solution to the lithium metal mixture there was added 0.161 g (0.00183 m) MTBE and the mix heated to near reflux (approx. 34° C.). About 1 ml of the t-butyl chloride feed solution was added at 33.5° C. which gave an exotherm in about 2 minutes. After 5 minutes the reaction temperature began to fall and a dropwise addition of the feed solution was begun. (Note: Although a container was placed under the reactor for safety purposes, no cooling bath was employed. The exothermic reaction was cooled by reflux).

The total addition time was 2.0 hours. The maximum reflux temperature observed was 36.9° C. and the final reflux temperature was 34.0° C. at the end of the feed. The reaction mixture was stirred 3 hours after the feed was complete.

The mixture was then pumped through a ⅜" teflon tube to a pressure filter (no filter aid) and filtered under an argon atmosphere. This filtration took 2 minutes. The reactor was then rinsed with 3×50 ml pentane each time and the rinses transferred to the muds which were also washed with the rinse, mixed and filtered. The final product was 282.2 g of a colorless solution. Analysis indicated a 88.3% yield of active R-Li (16.97 wt %) and a 89.6% yield of total base (17.22 wt %) based on moles of t-butyl chloride added.

EXAMPLE 4

Preparation of t-Butyllithium in Heptane Employing 1 mole percent of Methyl tert-butyl (MTBE)

To the usual 500 ml Morton/Cleaved reactor setup, described in Example 2, under argon atmosphere, was added 13.79 g (1.98 m) of lithium powder and 150 ml heptane. Next 10 ml of 1.75 molar t-butyllithium solution in pentane was added via syringe to the metal mixture and stirred to condition the reactor and metal surface.

Meanwhile, to the dropping funnel was added 76.53 g (0.8267 m) g-butyl chloride, 80 ml heptane, and 0.805 g (0.00913 m) MTBE. (Note: It is important to thoroughly mix the contents of the dropping funnel to give a uniform solution.) Immediately before beginning the addition of the t-butyl chloride solution, the lithium metal solvent mixture was heated to 38° C. About 1 ml of the t-butyl chloride solution was added at 38.0° C. which gave an exotherm in about 30 seconds. After 3 minutes the reaction temperature began to fall and a dropwise addition of the feed solution was begun. A cooling bath (~18° C.) of hexane to which dry ice was added periodically was employed to maintain a reaction temperature between 35° to 40° C.

The total addition time was 1.7 hours. No reflux was observed. The reaction mixture was stirred 3½ hours after the halide feed was complete.

The total addition time was 1.7 hours. No reflux was observed. The reaction mixture was stirred 3½ hours after the halide feed was complete.

The mixture was then pumped through a ⅜" teflon tube to a pressure filter (no filter aid) and filtered under an argon atmosphere. This filtration took 4 minutes. The reactor was then rinsed with a 3×50 ml heptane each time and the rinses transferred to the muds in the filter which were also washed with the rinse, mixed and filtered. The final product was 305.2 g of colorless solution. The slight haziness was caused by fine solids passing through the filter. Analysis of a sample of the clear solution indicated a 87.0% yield of active R-La (15.10 wt %) and a 89.1% yield of total base (15.46 wt %) based on moles of t-butyl chloride added.

EXAMPLE 5

Preparation of t-Butyllithium in Pentane Employing 1 mole percent of Di-n-octyl Ether (DOE)

To the reactor setup described in Example 2, under argon atmosphere, was added 16.20 g (2.33 m) lithium powder and 170 ml pentane. The lithium dispersion used in this reaction was the same as that used in Example 2. Next 10 ml of 1.8M t-butyllithium solution was added via syringe to the metal mixture and stirred to condition the reactor and metal surface.

Meanwhile, to the dropping funnel was added 89.73 g (0.969 m) t-butyl chloride, 100 ml pentane, and 2.275 g (0.00938 m) DOE. (Note: It is important to thoroughly mix the contents of the dropping funnel to give a uniform solution.) Before beginning the addition of the t-butyl chloride feed solution, the lithium metal mixture was heated to near reflux (approx. 34° C.). About 1 ml of the t-butyl chloride feed solution was added at 32.7° C. which gave an exotherm in about 1 minute. After 3 minutes the reaction temperature began to fall and a dropwise addition of the feed solution was begun. (Note: Although a container was placed under the reactor for safety purposes, no cooling path was employed.

The exothermic reaction was cooled by reflux off the cold finger condenser (dry ice/hexane)).

The total t-butyl chloride addition time was 2½ hours. The maximum reflux temperature observed was 36.4° C. and the final reflux temperature was 34.0° C. at the end of the feed. The reaction mixture was stirred 1 hour 24 minutes after the feed was complete.

The mixture was then pumped through a ⅜" teflon tube to a pressure filter (no filter aid) and filtered under an argon atmosphere. This filtration took 2 minutes. The reactor was then rinsed with 3×50 ml pentane each time and the rinses transferred to the muds which were also washed with the rinse and filtered. The final product was 309.9 g of hazy colorless suspension. The haziness was caused by fine solids passing through the filter. Analysis of a clear sample indicated an 87.5% yield of active R-Li (17.52 wt %) and an 88.2% yield of alkaline product (17.67 wt %) based on moles of t-butyl chloride added.

EXAMPLE 6

Preparation of 2-Ethylhexyllithium in Pentane Employing Methyl tert-Butyl Ether as Catalyst Lithium metal (19.64 g, 2.83 moles) in powder form containing 0.66% of alloyed sodium was transferred to a flask with the aid of 300 ml of dry pentane. Ten (10) ml of a 0.77M (7.7 millimoles) of 2-ethylhexyllithium in pentane was added as a conditioner and the mixture stirred for 30 minutes. A weight of 0.79 grams of dry methyl tert-butyl ether (1.0 mole % based on 2-ethylhexyl chloride) was added to the flask and the contents heated to reflux. Two 2 ml quantities from a total charge of 123.9 g (0.81 moles) of 2-ethylhexyl chloride were then added to initiate the reaction. No further heating was required while the remainder of the 2-ethylhexyl chloride was added at a constant rate over a period of 155 minutes. A constant rate of reflux was maintained throughout the halide feed. The reaction temperature rose from 35.3° to 39.8° C. during this time and then dropped off at completion of the halide addition. The reaction mixture was then stirred slowly overnight and filtered to obtain 249.9 grams of a hazy solution.

| Analytical Results: | |
|---|---|
| Total Base = | 37.90 wt % |
| Active Assay = | 37.59 wt % |
| Yield = | 96.6% |

COMPARATIVE EXAMPLE*

2-Ethylhexyllithium Preparation Employing Sodium Example 300-58

Procedures

Lithium dispersion (2.16 moles) was washed in a glass filter funnel with two 100 ml aliquots of pentane and then transferred to the reaction vessel along with 500 ml pentane. The reaction was initiated with n-butyl chloride (1.5 g) as evidenced by a temperature rise of 5.3° C. The reaction mass was stirred for seven minutes and then 2-ethylhexyl chloride (2 g) was added. After noting no evidence of reaction (heat) after three minutes, 2-ethylhexyl chloride (1 g) was added again. Again, there was no evidence of reaction after an additional three minutes (Temp.=27° C.). The reaction mass was then brought to reflux (35.9° C.), and more 2-ethylhexyl chloride (2 g) was added. The reflux quickly subsided, and there was no evidence of reaction after stirring for an additional three hours. Attempts to initiate the reaction with 2-ethylhexyl chloride (3 g) failed during the next two hours. Next, sodium dispersion in oil (containing 0.97 mole Na) was transferred to the reaction vessel and stirred for 10 minutes. This time the addition of 2-ethylhexyl chloride (1 g) resulted in immediate reaction as evidenced by a rise in temperature of 4° C. The remaining 2-ethylhexyl chloride (114 g) was added over a period of 166 minutes while maintaining the reaction temperature at reflux. The reaction mass was stirred for an additional two hours and then filtered. Filtration was rapid yielding a yellow solution of 2-ethylhexyllithium in pentane.

from our copending application U.S. Ser. NO. 749245 filed Aug. 22, 1991.

| Analytical Results: | |
|---|---|
| Total Base = | 1.87M |
| Active Assay = | 1.86M |
| Li (ICP) = | 1.76M |
| Na (ICP) = | 1 ppm |
| Inorganic chloride = | 610 ppm |
| NMR = | 1.89M |
| Yield = | 88.4% recovered |

This run shows that lithium containing alloying amounts of sodium (0.75% by weight) does not react with 2-ethylhexyl chloride in refluxing pentane.

EXAMPLE 7

Preparation of Isopropyllithium using Methyl tert-Butyl Ether as Catalyst

Lithium powder (16 grams, 2.31 moles) was transferred to a reaction vessel with 3 portions of 100 ml each of pentane and the mixture heated to reflux. A weight of 0.85 g(0.0096 m) of methyl tert-butyl ether was mixed with 75.4 g (0.96 mole) of isopropyl chloride in an addition funnel, and the mixture added dropwise to the metal suspension while maintaining reflux over a 2.5 hour period. After slow stirring overnight, the mixture was filtered and the muds washed twice with pentane. A volume of 400 ml (257.9 g) of a pale yellow solution was obtained with an assay of 15.7 wt % isopropyllithium. Yield—84.3%.

In a comparative experiment keeping all other factors the same except leaving out the methyl tert-butyl ether catalyst, the yield of isopropyllithium was only 79.2%.

TABLE 1

SYNTHESIS OF t-BUTYLLITHIUM EMPLOYING VARIOUS CATALYSTS

| Excess[1] mole % Li | Catalyst Added Name | mole %[3] | t-BuLi[3] Yield (%) |
|---|---|---|---|
| 20[2] | None | | 74.3 |
| 20 | di-n-octyl ether | 1.87 | 89.3 |
| 21 | di-n-octyl ether | 1.00 | 89.0 |
| 20 | di-n-octyl ether | 0.64 | 88.1 |
| 20 | di-n-octyl ether | 0.25 | 83.5 |
| 21 | di-n-octyl ether | 0.12 | 79.5 |
| 21 | di-n-hexyl ether | 1.02 | 87.8 |
| 20 | di-n-hexyl ether | 0.51 | 87.1 |

TABLE 1-continued

SYNTHESIS OF t-BUTYLLITHIUM EMPLOYING VARIOUS CATALYSTS

| Excess[1] mole % Li | Catalyst Added Name | mole %[3] | t-BuLi[3] Yield (%) |
|---|---|---|---|
| 20 | methyl t-butyl ether | 1.0 | 96 |
| 20 | diazabicyclo-octane | 1.11 | 81 |
| 20 | N,N,N',N'-tetramethyl-ethylenediamine | 1.02 | 81 |

[1]Same lot of lithium dispersion (containing 0.57% Na on Li) employed for all Examples shown in this Table. Excess lithium based on the amount of t-butyl chloride employed.
[2]Standard run employing commercial t-butyl chloride containing t-butyl alcohol impurity.
[3]Mole % added and recovered yields based on t-butyl chloride.

TABLE 2

COMPARATIVE YIELDS OF RLi USING MTBE AS CATALYST

| RLi Type | MTBE Catalyst* Added | Yield (%) |
|---|---|---|
| t-Butyllithium | None | 43 |
| | 1.0 | 98 |
| Isopropyllithium | None | 79 |
| | 1.0 | 84 |
| 2-Ethylhexyllithium | None | 0 |
| | 1.0 | 97 |
| n-Hexyllithium | None | 74 |
| | 1.0 | 78 |
| 3-Methyl-3-lithio-pentane | None | 0 |
| | 1.0 | 18 |

*mole %

TABLE 3

| Exp. No. | t-BuCl moles | Li mol % xs. | Wt % t-BuOH in t-BuCl | Catalyst added Type | Mol % | Th. Conc. t-BuLi (wt %) | % Yield |
|---|---|---|---|---|---|---|---|
| 7552 | 0.661 | 19.5 | 0.00 | None | | 24.8 | 42.7 |
| 7553 | 0.961 | 20.7 | 0.00 | MTBE | 0.98 | 25.6 | 94.6 |
| 7560 | 0.843 | 19.8 | 0.21 | None W. N. Smith U.S. Pat. No. 3,420,903 | | 26.0 | 62.4 |
| Ex. 2 | 0.50 | 28 | 0.00 | None | | 17.0 | 40.0 |
| Ex. 3 | 0.50 | 28 | 0.00 | t-BuOH | 0.62 | 17.0 | 74.2 |
| Ex. 4 | 0.50 | 28 | 0.00 | t-BuOH | 1.9 | 17.0 | 74.0 |

TABLE 4

SYNTHESIS OF t-BUTYLLITHIUM EMPLOYING ETHER CATALYSTS

| Catalyst | Mole % | Solvent | Excess Li mole % | Yield % |
|---|---|---|---|---|
| Di-n-octyl ether | 1.0 | Pentane | 20 | 88 |
| | 0.2 | Pentane | 20 | 84 |
| | 1.0 | Heptane | 20 | 70 |
| Methyl tert-Butyl Ether | 1.0 | Pentane | 20 | 98 |
| | 1.0 | Pentane | 10 | 90 |
| | 0.2 | Pentane | 20 | 90 |
| | 1.0 | Heptane | 20 | 89 |
| Tetrahydrofuran | 1.0 | Pentane | 40 | 90 |
| | 1.0 | Pentane | 10 | 73 |
| Ethyl Ether | 1.0 | Pentane | 20 | 90 |
| 2-Ethoxyethyl Ether | 1.0 | Pentane | 20 | 85 |

TABLE 5

SYNTHESIS t-BUTYLDIMETHYLCHLOROSILANE (TBSCL) EMPLOYING VARIOUS AMOUNTS OF ETHERS

| Example Number | t-BuLi moles | DMDCS[1] moles | Ether type | Ether moles | TBSCL[2] Yield % |
|---|---|---|---|---|---|
| B[6] | 0.103 | 0.103 | THF[3] | 0.3690 | 16.3 |
| C | 0.103 | 0.103 | THF | 0.103 | 34.2 |
| 5 | 1.00 | 1.02 | THF | 0.0112 | 97.8 |
| D | 0.103 | 0.103 | DOE[4] | 0.103 | 65.9 |
| 6 | 0.944 | 0.960 | DHE[5] | 0.0119 | 100 |
| 8 | 3.47 | 3.55 | DHE | 0.05 | 100[7] |

[1]Dimethyldichlorosilane
[2]Yield determined by GLC
[3]Tetrahydrofuran
[4]Di-n-Octyl ether
[5]Di-n-Hexyl ether
[6]Examples B, C, and D are Comparison Examples (see copending application filed on even date herewith)
[7]t-Butyltrichlorosilane

TABLE 6

THERMAL STABILITY OF TERTIARY BUTYLLITHIUM WITH AND WITHOUT ETHER CATALYST ADDITIVES

| Experiment Number | Conc.[1] M | Temp °C. | Number Days | Catalyst[2] Name | % | % lost | Av % C—Li[3] lost/day | Av % T. Base[4] lost/day |
|---|---|---|---|---|---|---|---|---|
| Comparison | 1.41 | 0 | 59 | none | | | 0 | 0 |
| | | 15 | 30 | | | | 0 | 0 |
| | | 40 | 32 | | | | 0.09[5] | 0 |
| 7370 | 1.94 | 0 | 45 | DOE | 0.64 | 24 | 0 | 0 |
| | | 15 | 30 | | | 0 | 0 | 0 |
| | | 40 | 28 | | | 31 | 0.26 | 0.29 |
| 7356 | 1.53 | 0 | 45 | DOE | 1.00 | 18 | 0 | 0 |
| | | 40 | 28 | | | 31 | 0.40 | 0.37 |
| 7375 | 1.87 | 0 | 45 | DOE | 1.87 | 29 | 0 | 0 |
| | | 15 | 30 | | | 6 | 0 | 0 |
| | | 40 | 28 | | | 46 | 0.48 | 0.54 |
| 7494 | 1.99 | 40 | 32 | MTBE | 0.93 | 82 | 0.06 | 0.06 |
| | | 15 | 62 | | | 64 | 0 | 0 |
| 7503[6] | 1.63 | 40 | 30 | MTBE | 1.10 | 97 | 0.08 | 0.12 |
| | | 40 | 60 | | | 100 | 0.09 | 0.10 |
| | | 15 | 30 | | | 76 | 0 | 0 |
| | | 15 | 60 | | | 85 | 0 | 0 |

TABLE 6-continued

THERMAL STABILITY OF TERTIARY BUTYLLITHIUM WITH AND WITHOUT ETHER CATALYST ADDITIVES

| Experiment Number | Conc.[1] M | Temp °C. | Number Days | Catalyst[2] Name | % | % lost | Av % C—Li[3] lost/day | Av % T. Base[4] lost/day |
|---|---|---|---|---|---|---|---|---|
| | | | 0 | | 60 | | 73 | 0 | 0 |

[1] Active C—Li concentration at the start of the test.
[2] TBL was prepared with this catalyst. % = mole % catalyst based on t-butyl chloride.
[3] The average % carbon-bound lithium lost/day was based on $V_2O_5$ analyses.
[4] The average % total alkalinity loss/day was based on total base analyses and indicates the amount of basic material loss by precipitation.
[5] Data indicates a 0.015%/mo (0.0005%/day) at 20° C. for 15 wt % TBL in pentane (see Chemetal Data Sheet).
[6] TBL in heptane.

TABLE 7

| Effect of loss of t-BuLi yield on RMC of alkylated product | | | | |
|---|---|---|---|---|
| 100% | 95% | 90% | 85% | 80% |
| 0 | 3.7% | 7.8% | 12.5% | 17.8% |

RMC = raw material cost

We claim:

1. A process for alkylating an alkali metal selected from lithium, sodium and potassium with an alkyl halide containing 3 to 20 carbon atoms in which the improvement comprises conducting the reaction in a hydrocarbon solvent in the presence of a catalyst compound represented by the formula $(RR^1R^2M^a)yA(R^3)x$ wherein R, $R^1$ and $R^2$ are independently selected from hydrogen, halogen, alkyl, and alkenyl groups containing 1 to 13 carbon atoms, cycloalkyl groups containing 3 to 10 carbon atoms, aryl groups containing 6 to 18 carbon atoms, $R^3$ is independently selected from aryl groups containing 6 to 18 carbon atoms, four to six-membered heterocyclic carbon containing groups containing one to two hetero atoms selected from oxygen, nitrogen, and sulfur; hydroxyalkyl, alkoxyalkyl and monoalkylaminoalkyl and dialkylaminoalkyl groups containing 2 to 13 carbon atoms; $M^a$ is selected from silicon, carbon, germanium, and tin, A is selected from oxygen, sulfur, nitrogen and phosphorus, and x and y independently have values from zero to three.

2. The process of claim 1 wherein the compound $(RR^1R^2M^a)yA(R^3)x$ is a cyclic ether wherein A is oxygen and $R^3$ is a tetramethylene radical.

3. The process of claim 2 wherein the cyclic ether is selected from the group consisting of tetrahydrofuran and methyltetrahydrofuran.

4. The process of claim 1 wherein the compound $(RR^1R^2M^a)yA(R^3)x$ is a bis-hydrocarbyl ether, wherein $M^a$ is carbon, A is oxygen, and x+y is two.

5. The process of claim 4 wherein the bis-hydrocarbyl ether is selected from the group of diethyl ether, dimethyl ether, methyl-t-butyl ether, di-n-butyl ether, diamyl ether, di-n-hexyl ether, di-n-octyl ether, and the dimethyl ether of diethylene glycol.

6. The process of claim 4 wherein the compound $(RR^1R^2M^a)yA(R^3)x$ is a mixed hydrocarbylsilyl ether wherein R, $R^1$, $R^2$, and $R^3$ have meanings as described above, $M^a$ is silicon, A is oxygen, and x and y are one.

7. The process of claim 6 wherein the hydrocarbyl silyl ether is selected from the group consisting of chlorodimethylisopropoxysilane, trimethylisopropoxysilane, methyldichloroisopropoxysilane, and t-butyldimethylisopropoxysilane.

8. The process of claim 1 wherein the compound $(RR^1R^2M^a)yA(R^3)x$ is a tris-hydrocarbylamine, wherein $M^a$ is carbon, A is nitrogen, and x+y is three.

9. The process of claim 8 wherein the tris-hydrocarbylamine is selected from the group of triethylamine, triethylamine, trihexylamine, trimethylamine, methyldibutylamine, tetramethylethylenediamine, and pentamethylethylenetriamine.

10. A process of producing an alkyllithium by reacting lithium with a hindered alkyl chloride in which the hindered alkyl group is selected from t-butyl, and 2-ethylhexyl groups in which the improvement comprises conducting the reaction in the presence of 0.02 to 5.0 mole percent of a compound selected from hydrocarbyl ethers containing 2 to 16 carbon atoms in a hydrocarbon solvent.

11. The process of claim 10 wherein the hindered alkyl halide is t-butyl chloride and the hydrocarbyl ether is di-n-octyl ether.

12. The process of claim 10 wherein the hindered alkyl halide is t-butyl chloride and the hydrocarbyl ether is tetrahydrofuran.

13. The process of claim 10 wherein the hindered alkyl halide is t-butyl chloride, the hydrocarbyl ether is methyl tert-butyl ether and the hydrocarbon solvent is hexane, pentane, or heptane, ether is tetrahydrofuran.

* * * * *